United States Patent
Sasaki et al.

(10) Patent No.: US 9,579,266 B2
(45) Date of Patent: *Feb. 28, 2017

(54) OIL IN WATER EMULSION COSMETIC COMPOSITION FOR SKIN

(75) Inventors: Kazutaka Sasaki, Yokohama (JP);
Manabu Shimoda, Yokohama (JP);
Yoshihito Takakura, Yokohama (JP);
Haruhiko Inoue, Yokohama (JP);
Shigeru Mugikura, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/003,317

(22) PCT Filed: Jul. 8, 2009

(86) PCT No.: PCT/JP2009/062425
§ 371 (c)(1),
(2), (4) Date: Jul. 28, 2011

(87) PCT Pub. No.: WO2010/005020
PCT Pub. Date: Jan. 14, 2010

(65) Prior Publication Data
US 2011/0275712 A1 Nov. 10, 2011

(30) Foreign Application Priority Data
Jul. 9, 2008 (JP) ................................. 2008-179538

(51) Int. Cl.
| | |
|---|---|
| *A61K 8/06* | (2006.01) |
| *A61K 31/53* | (2006.01) |
| *A61K 31/216* | (2006.01) |
| *A61K 31/277* | (2006.01) |
| *A61Q 17/04* | (2006.01) |
| *A61K 8/34* | (2006.01) |
| *A61K 8/37* | (2006.01) |
| *A61K 8/67* | (2006.01) |
| *A61K 8/86* | (2006.01) |
| *A61Q 19/08* | (2006.01) |

(52) U.S. Cl.
CPC ................. *A61K 8/06* (2013.01); *A61K 8/062* (2013.01); *A61K 8/342* (2013.01); *A61K 8/375* (2013.01); *A61K 8/671* (2013.01); *A61K 8/86* (2013.01); *A61Q 19/08* (2013.01)

(58) Field of Classification Search
USPC ...................... 424/60, 59; 514/246, 506, 519
IPC ........... A61K 8/06,8/062, 8/342, 31/53, 31/216, 31/277; A61Q 17/04
See application file for complete search history.

(56) References Cited

U.S. PATENT DOCUMENTS

| | | | | |
|---|---|---|---|---|
| 5,916,543 A * | 6/1999 | Kaplan | .......................... | 424/59 |
| 5,948,416 A * | 9/1999 | Wagner et al. | ............... | 424/401 |
| 5,976,555 A * | 11/1999 | Liu et al. | ...................... | 424/401 |
| 6,210,693 B1 * | 4/2001 | Inoue et al. | .................. | 424/401 |
| 6,241,993 B1 * | 6/2001 | Breton et al. | ................. | 424/401 |
| 2003/0165546 A1 | 9/2003 | Resch et al. | | |

FOREIGN PATENT DOCUMENTS

| | | | |
|---|---|---|---|
| EP | 2181697 | * | 5/2010 |
| JP | 2005-104962 | | 4/2005 |
| JP | 2005-320263 | | 11/2005 |

OTHER PUBLICATIONS

International Search Report for corresponding PCT/JP2009/062425, mailed Oct. 13, 2009, three pages.

* cited by examiner

*Primary Examiner* — Shirley V Gembeh
(74) *Attorney, Agent, or Firm* — Rankin, Hill & Clark LLP

(57) ABSTRACT

An oil in water emulsion cosmetic composition for skin, in which vitamin A and its derivatives are stably incorporated and which has superior feeling in use (skin familiarity or feeling of skin absorption, feeling of efficacy after application) and base composition stability (emulsion stability) with the passage of time. The oil in water emulsion cosmetic composition for skin comprises, relative to the total amount of the cosmetic composition, (a) from 0.01 to 4% by mass of vitamin A and its derivative, (b) from 0.6 to 4% by mass of a nonionic surfactant comprising three of (b-1) sorbitan tristearate, (b-2) polyethylene glycol stearate with from 20 to 120 mols of polyethylene glycol added thereto, (b-3) glyceryl stearate having an HLB of from 5 to 8, and (c) from 1 to 10% by mass of a higher alcohol having from 14 to 24 carbon atoms, wherein the blend ratio (by mass) of component (b-1) to component (b) is from 0.1 to 0.8.

15 Claims, No Drawings

OIL IN WATER EMULSION COSMETIC COMPOSITION FOR SKIN

TECHNICAL FIELD

The present invention relates to an oil in water emulsion cosmetic composition for skin. More precisely, the invention relates to an oil in water emulsion cosmetic composition for skin, especially to a cream type one, in which vitamin A and its derivatives are stably incorporated and which has superior feeling in use (skin familiarity or feeling of skin absorption, feeling of efficacy after application) and base composition stability (emulsion stability) with the passage of time.

BACKGROUND ART

Vitamin A and its derivatives (=retinols), such as typically vitamin A and vitamin A acetate or the like, have heretofore been known as ingredients effective for prevention or remedy for skin keratosis and for prevention or recovery of skin aging, and are incorporated as active ingredients in external preparations for skin.

However, vitamin A and its derivatives are unstable and are readily denatured by the influence of light, air, heat, metal ions and the like thereon. Accordingly, external preparations for skin with such vitamin A and its derivatives incorporated therein have a problem in the stability with the passage of time thereof. Heretofore, for solving the problems, there has been reported a technique of incorporating an oil-soluble antioxidant thereinto. For example, JP 11-228377A (Patent Reference 1) discloses an oil in water emulsion composition containing a vitamin A fatty acid ester, an oil-soluble antioxidant, an amphiphilic substance, and a hydrophilic nonionic surfactant in a specific blend ratio. JP 2005-104962A (Patent Reference 2) discloses an external preparation for skin containing vitamin and/or its derivative, a chemical having a superoxide removal rate of at least 75% and an oil-soluble antioxidant.

The invention described in Patent Reference 1 exhibits an excellent effect for stable incorporation of vitamin A and its derivatives, however, it has made no investigation for the feeling in use (skin familiarity, feeling of efficacy after application) in particular. Patent Reference 2 also does not have a description relating to the effect of feeling in use.

JP 2005-320263A (Patent Reference 3) discloses an oil in water emulsion cosmetic composition for skin, especially a cream-type one for which the feeling in use such as fittability, permeability and the like, is aspired for; however, the patent publication does neither describe nor suggest stable storage of vitamin A and its derivatives.

PRIOR ART REFERENCES

Patent References

Patent Reference 1: JP 11-228377A
Patent Reference 2: JP 2005-104962A
Patent Reference 3: JP 2005-320263A

SUMMARY OF THE INVENTION

Problems that the Invention is to Solve

The present invention has been made in consideration of the above-mentioned situation, and its object is to provide an oil in water emulsion cosmetic composition for skin, in which vitamin A and its derivatives are stably incorporated and which has superior feeling in use (skin familiarity or feeling of skin absorption, feeling of efficacy after application) and base composition stability (emulsion stability) with the passage of time.

Means for Solving the Problems

To solve the above-mentioned problems, the invention provides an oil in water emulsion cosmetic composition for skin comprising, relative to the total amount of the cosmetic composition,
  (a) from 0.01 to 4% by mass of vitamin A and its derivative;
  (b) from 0.6 to 4% by mass of a nonionic surfactant comprising the following components (b-1) to (b-3):
    (b-1) sorbitan tristearate,
    (b-2) polyethylene glycol stearate with from 20 to 120 mols of polyethylene glycol added thereto,
    (b-3) glyceryl stearate having an HLB of from 5 to 8,
  (c) from 1 to 10% by mass of a higher alcohol having from 14 to 24 carbon atoms;
  wherein the blend ratio (by mass) of component (b-1) to component (b) is from 0.1 to 0.8.

Advantage of the Invention

The oil in water emulsion cosmetic composition for skin of the invention is excellent in stable incorporation of vitamin A and its derivatives therein, in feeling in use (skin familiarity or feeling of skin absorption, feeling of efficacy after application) and in base composition stability (emulsion stability) with the passage of time.

MODE FOR CARRYING OUT THE INVENTION

The invention is described in detail hereinunder.

Vitamin A and its derivative as component (a) include vitamin A (=retinol), vitamin A aldehyde (=retinal), vitamin A acid (=retinoic acid), vitamin A fatty acid ester, and their salts. The vitamin A fatty acid esters include vitamin A acetate (=retinol acetate), vitamin A palmitate (=retinol palmitate), vitamin A propionate (=retinol propionate), and vitamin A linolate (=retinol linolate). The salts include alkali metal salts (for example, sodium salts, potassium salts, and lithium salts), alkaline earth metal salts (for example, calcium salts, and magnesium salts), ammonium salts, organic amine salts (for example, monoethanolamine salts, diethanolamine salts, and triethanolamine salts). In the invention, as component (a), especially preferred are vitamin A fatty acid esters and their salts from the viewpoint of the stability, the efficacy, etc. One or more may be used as component (a).

The amount of component (a) is from 0.01 to 4% by mass in the oil in water emulsion cosmetic composition for skin of the invention, preferably from 0.1 to 0.5% by mass. When the amount is less than 0.01% by mass, component (a) could not sufficient exhibit the pharmaceutical efficacy thereof; but when more than 4% by mass, the ingredient may produce excessive irritation to skin.

Component (b) is a nonionic surfactant, and in the invention, this comprises the following components (b-1), (b-2) and (b-3) as the indispensable ingredients.

Component (b-1) is sorbitan tristearate. Its HLB is 2.1 and it is oleophilic.

Component (b-2) is polyethylene glycol stearate with from 20 to 120 mols of polyethylene glycol added thereto. Concretely, it includes polyethylene glycol monostearate (20 polyethylene glycol adduct—this may be represented by 20EO or 20PG, and the same shall apply hereinunder), polyethylene glycol monostearate (25EO), polyethylene glycol monostearate (30EO), polyethylene glycol monostearate (40EO), polyethylene glycol monostearate (45EO), polyethylene glycol monostearate (55EO), polyethylene glycol monostearate (100EO), etc.; however, the invention is not limited to these examples. Above all, preferred are polyethylene glycol monostearate (40EO), polyethylene glycol monostearate (45EO), and polyethylene glycol monostearate (55EO), from the viewpoint of the feeling in use. One or more may be used as component (b-2).

Component (b-3) is glyceryl stearate having an HLB of from 5 to 8. Component (b-3) is controlled to have an HLB of from 5 to 8 by mixing an arbitrary higher fatty acid in glyceryl stearate. It includes a self-emulsifying type prepared by adding soap and/or a nonionic surfactant to glyceryl stearate. Concretely, there are mentioned glyceryl stearate (HLB 5), self-emulsifying glyceryl stearate (HLB 5), self-emulsifying glyceryl stearate (HLB 6), self-emulsifying glyceryl stearate (HLB 7), glyceryl isostearate (HLB 6), glyceryl diisostearate (HLB 3), etc. One or more may be used as component (b-3).

HLB is computed according to the Kawakami formula represented by the following numerical formula 1:

$$HLB=7+11.7\cdot\log(MW/MO) \qquad \text{[Numerical Formula 1]}$$

(wherein MW represents the molecular weight of the hydrophilic group moiety; and MO represents the molecular weight of the oleophilic group moiety).

The amount (total amount) of component (b) is from 0.6 to 4% by mass in the oil in water emulsion cosmetic composition for skin of the invention, preferably from 1 to 3% by mass. When the amount is less than 0.6% by mass, the ingredient could not secure a sufficient emulsifying force and therefore the base composition stability with the passage of time may be poor; but on the other hand, when more than 4% by mass, component (a) could not be stably incorporated.

In the present invention, the blend ratio (by mass) of component (b-1) to the total amount of component (b) is from 0.1 to 0.8 as component (b-1)/component (b). When the blend ratio of component (b-1)/component (b) oversteps the above range, then the effect of stably incorporating component (a) could not be secured.

Component (c) is a higher alcohol having from 14 to 24 carbon atoms, preferably from 16 to 22 carbon atoms. Concretely, it includes linear alcohols, such as cetyl alcohol, stearyl alcohol, behenyl alcohol, myristyl alcohol, oleyl alcohol, and cetostearyl alcohol; branched alcohols, such as monostearyl glycerin ether (batyl alcohol), 2-decyltetradecinol, lanolin alcohol, hexyl-dodecanol, isostearyl alcohol, and octyldodecanol. Above all, preferred are stearyl alcohol and behenyl alcohol. One or more may be used as component (c).

The amount of component (c) is from 1 to 10% by mass in the oil in water emulsion cosmetic composition for skin of the invention, preferably from 2 to 5% by mass. When the amount is less than 1% by mass and when the base is cream, a dissociation may occur, and it is hard to obtain skin familiarity in point of the feeling in use of the preparation; but on the other hand, when the amount is more than 10% by mass, the preparation may be sticky and its feeling in use may worsen.

The oil in water emulsion cosmetic composition for skin of the invention containing the above components (a) to (c) can keep component (a) stably therein and is excellent in the feeling in use (skin familiarity or feeling of skin absorption, feeling of efficacy after application) and the stability (emulsion stability) with the passage of time.

The oil in water emulsion cosmetic composition for skin of the invention can be prepared according to an ordinary method, and the emulsification method for it is not specifically defined. For example, there may be mentioned a method of individually heating the oily phase (inner phase) and the aqueous phase (outer phase) at around 70° C., then gradually adding the heated oily phase to the aqueous phase, emulsifying it with an emulsifying machine, and thereafter leaving it cooled to room temperature, but not limited thereto. In general, the aqueous phase (outer phase) is preferably from 20 to 80% by mass relative to the total amount of the cosmetic composition, more preferably from 30 to 60% by mass.

The oil in water emulsion cosmetic composition for skin of the invention includes emulsion products, such as emulsion foundation, sun-block emulsion, and beauty essence; as well as cream products such as skin cream, etc.; but not limited to thereto.

Within a range not detracting from the advantage of the invention, any optional additive ingredients generally used in external applications for skin, such as ordinary cosmetic compositions, pharmaceutical preparations and others, for example, powdery ingredient, solid oil and fat, wax, hydrocarbon, higher fatty acid, ester, silicone, anionic surfactant, cationic surfactant, ampholytic surfactant, nonionic surfactant (except component (b)), water-soluble polymer, UV absorbent, metal ion scavenger, lower alcohol, polyalcohol, sugar, amino acid, organic acid, polymer emulsion, pH regulator, skin nutrient, vitamin, antioxidant, antioxidation promoter, fragrance, water and others may be, if desired, suitably incorporated in the oil in water emulsion cosmetic composition for skin of the invention.

The powder ingredients include inorganic powders, such as talc, kaolin, mica, sericite, muscovite, phlogopite, synthetic mica, lepidolite, biotite, vermiculite, magnesium carbonate, calcium carbonate, aluminium silicate, barium silicate, calcium silicate, magnesium silicate, strontium silicate, metal tungstate, magnesium, silica, zeolite, barium sulfate, fired calcium sulfate (burnt plaster), calcium phosphate, fluoroapatite, hydroxyapatite, ceramic powder, metal soap (e.g., zinc myristate, calcium palmitate, aluminium stearate), and boron nitride; organic powders, such as polyamide resin powder (nylon powder), polyethylene powder, polymethyl methacrylate powder, polystyrene powder, styrene/acrylic acid copolymer resin powder, benzoguanamine resin powder, polytetrafluoroethylene powder, and cellulose powder; inorganic white pigments, such as titanium dioxide, and zinc oxide; inorganic reddish pigments, such as iron oxide (Bengal red), and iron titanate; inorganic brownish pigments such as γ-iron oxide; inorganic yellowish pigments, such as yellow iron oxide, and ocher; inorganic blackish pigments, such as black iron oxide, and low-order titanium oxide; inorganic violetish pigments, such as mango violet, and cobalt violet; inorganic greenish pigments, such as chromium oxide, chromium hydroxide, and cobalt titanate; inorganic bluish pigments, such as ultramarine, and prussian blue; pearl pigments, such as titanium oxide-coated mica, titanium oxide-coated bismuth oxychloride, titanium oxide-coated talc, colored titanium oxide-coated mica, bismuth oxychloride, and fish scale foil; metal powder pigments, such as aluminium powder, and copper powder; zirconium, barium or aluminium lake organic pigments (e.g., organic pigments, such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, Blue No. 404, etc.; as well as Red. No. 3, Red. No. 104, Red. No. 106, Red. No. 227, Red. No. 230, Red. No. 401, Red. No. 505, Orange No. 205, Yellow No. 4, Yellow No. 5, Yellow No. 202, Yellow No. 203, Green No. 3, Blue No. 1, etc.); natural colorants, such as chlorophyll, and β-carotene.

The solid fats and oils include cacao butter, coconut oil, horse fat, hardened coconut oil, palm oil, beef tallow, mutton tallow, hardened beef tallow, palm kernel oil, lard, beef bone tallow, Japanese core wax, hardened oil, neatsfoot tallow, Japanese wax, and hardened castor oil.

The waxes include bees wax, candelilla wax, cotton wax, carnauba wax, bayberry wax, tree wax, whale wax, montan wax, bran wax, lanolin, kapok wax, lanolin acetate, liquid lanolin, sugar cane wax, lanolin fatty acid isopropyl ester, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol, and POE hydrogenated lanolin alcohol ether.

The higher fatty acids include lauric acid, myristic acid, palmitic acid, stearic acid, behenic acid, oleic acid, undecylenic acid, tall oil acid, isostearic acid, linoleic acid, linolenic acid, eicosapentaenoic acid (EPA), and docosahexaenoic acid (DHA).

The anionic surfactants include fatty acid soaps, such as sodium laurate, and sodium palmitate; higher alkylsulfate salts, such as sodium laurylsulfate, and potassium lauryl sulfate; alkyl ether sulfate salts, such as triethanolamine POE-laurylsulfate, and sodium POE-laurylsulfate; n-acyl sarcosine acids, such as sodium lauroylsarcosine; higher fatty acid amide sulfonates, such as sodium N-myristoyl-N-methyltaurine, coconut oil fatty acid methyltaurid sodium salt, and laurylmethyltaurid sodium salt; phosphate salts, such as sodium POE oleyl ether phosphate, and POE stearyl ether phosphoric acid; sulfosuccinate salts, such as sodium di-2-ethylhexylsulfosuccinate, sodium monolauroyl-monoethanolamide polyoxyethylene sulfosuccinate, and sodium laurylpolypropylene glycol sulfosuccinate; alkylbenzenesulfonate salts, such as sodium linear dodecylbenzenesulfonate, triethanolamine linear dodecylbenzenesulfonate, and linear dodecylbenzenesulfonic acid; higher fatty acid ester sulfate salts, such as hardened coconut oil fatty acid glycerin sulfate sodium salt; N-acylglutamate salts, such as monosodium N-lauroylglutamate, disodium N-stearoylglutamate, and monosodium N-myristoyl-L-glutamate; sulfated oils, such as turkey red oil; POE-alkyl ether carboxylic acids; POE-alkylaryl ether carboxylic acid salts; α-olefinsulfonic acid salts; higher fatty acid ester sulfonate salts; secondary alcohol sulfate salts; higher fatty acid alkylolamide sulfate salts; sodium lauroylmonoethanol-amidesuccinate; ditriethanolamine N-palmitoylaspartate; and casein sodium.

The cationic surfactants include alkyltrimethyl ammonium salts, such as stearyltrimethyl ammonium chloride, and lauryltrimethyl ammonium chloride; alkylpyridinium salts, such as cetylpyridinium chloride; distearyldimethylammonium dialkyldimethylammonium chloride; poly(N,N-dimethyl-3,5-methylenepyridinium) chloride; alkyl-quaternary ammonium salts; alkyldimethylbenzylammonium salts; alkylisoquinolinium salts; dialkylmorpholinium salts; POE-alkylamines; alkylamine salts; polyamine fatty acid derivatives; amyl alcohol fatty acid derivatives; benzalkonium chloride; and benzetonium chloride.

The ampholytic surfactants include imidazoline-type ampholytic surfactants, such as 2-undecyl-N,N,N-(hydroxyethylcarboxymethyl)-2-imidazoline sodium salt, and 2-cocoyl-2-imidazaliniumhydroxide-1-carboxyethyloxy-2-sodium salt; betaine-type surfactants, such as 2-heptadecyl-N-carboxymethyl-N-hydroxyethylimidazolinium betaine, betaine lauryldimethylamino-acetate, alkyl betaine, amide betaine, and sulfobetaine.

Examples of the lipophilic nonionic surfactants include sorbitan fatty acid esters, such as sorbitan monooleate, sorbitan monoisostearate, sorbitan monolaurate, sorbitan monopalmitate, sorbitan monostearate, sorbitan sesquioleate, sorbitan trioleate, diglycerolsorbitan penta-2-ethylhexanoate, and diglycerolsorbitan tetra-2-ethylhexanoate; glycerol polyglycerol fatty acids, such as mono-cottonseed-fatty acid glyceryl ester, glyceryl monoerucate, glyceryl sesquioleate, glyceryl monostearate, glyceryl α,α'-oleate pyroglutamate, and glyceryl monostearate malate; propylene glycol fatty acid esters, such as propylene glycol monostearate; hardened castor oil derivatives; and glycerol alkyl ethers.

Examples of the hydrophilic nonionic surfactants include POE-sorbitan fatty acid esters, such as POE-sorbitan monooleate, POE-sorbitan monostearate, POE-sorbitan monooleate, and POE-sorbitan tetraoleate; POE-sorbitol fatty acid esters, such as POE-sorbitol monolaurate, POE-sorbitol monooleate, POE-sorbitol pentaoleate, and POE-sorbitol monostearate; POE-glycerol fatty acid esters, such as POE-monooleates such as POE-glyceryl monostearate, POE-glyceryl monoisostearate, and POE-glyceryl triisostearate; POE-fatty acid esters, such as POE-distearate, and POE-monodioleate and ethylene glycol distearate; POE-alkyl ethers, such as POE-lauryl ether, POE-oleyl ether, POE-stearyl ether, POE-behenyl ether, POE-2-octyldodecyl ether, and POE-cholestanol ether; Pluronics such as Pluronic; POE/POP-alkyl ethers, such as POE/POP-cetyl ether, POE/POP-2-decyltetradecyl ether, POE/POP-monobutyl ether, POE/POP-hydrogenated lanolin, and POE/POP-glyceryl ether; tetra-POE/tetra-POP-ethylenediamine condensates, such as Tetronic; POE-castor oil/hardened castor oil derivatives, such as POE-castor oil, POE-hardened castor oil, POE-hardened castor oil monoisostearate, POE-hardened castor oil triisostearate, POE-hardened castor oil monopyroglutamate monoisostearate diester, and POE-hardened castor oil maleate; POE-bees wax/lanolin derivatives, such as POE-sorbitol bees wax; alkanolamides, such as coconut oil fatty acid diethanolamide, lauric acid monoethanolamide, and fatty acid isopropanolamide; POE-propylene glycol fatty acid esters; POE-alkylamines; POE-fatty acid amides; sucrose fatty acid esters; alkylethoxydimethylamine oxides; and trioleyl phosphate.

The natural water-soluble polymers include plant polymers, such as gum arabic, gum tragacanth, galactan, guar gum, carob gum, karaya gum, carrageenan, pectin, agar, quince seed (Cydonia oblonga), algae colloid (brown algae extract), starch (rice, corn, potato, wheat), and glycyrrhizic acid; microbial polymers, such as xanthan gum, dextran, succinoglucane, and pullulan; animal polymers, such as collagen, casein, albumin, and gelatin.

The semi-synthetic water-soluble polymers include starch-type polymers, such as carboxymethyl starch, and methylhydroxypropyl starch; cellulose-type polymers, such as methyl cellulose, ethyl cellulose, methylhydroxypropyl cellulose, hydroxyethyl cellulose, sodium cellulose sulfate, hydroxypropyl cellulose, carboxymethyl cellulose, sodium carboxymethyl cellulose, crystalline cellulose, and cellulose powder; alginic acid-type polymers, such as sodium alginate, and propyleneglycol alginate ester.

The synthetic water-soluble polymers include vinylic polymers, such as polyvinyl alcohol, polyvinyl methyl ether, polyvinyl pyrrolidone, and carboxyvinyl polymer; polyoxyethylene-type polymers, such as polyoxyethylene-polyoxypropylene copolymers with polyethylene glycol 20,000, 40,000 or 60,000; acrylic polymers, such as sodium polyacrylate, polyethyl acrylate, and polyacrylamide; polyethyleneimine; and cationic polymers.

The inorganic water-soluble polymers include bentonite, AlMg silicate (bee gum), laponite, hectorite, and silicic anhydride.

The UV absorbents include benzoic acid-type UV absorbents, such as paraminobenzoic acid (hereinafter abbreviated as PABA), PABA monoglyceryl ester, N,N-dipropoxy-PABA ethyl ester, N,N-diethoxy-PABA ethyl ester, N,N-dimethyl-PABA ethyl ester, N,N-dimethyl-PABA butyl ester, and N,N-dimethyl-PABA ethyl ester; anthranilic acid-type UV absorbents, such as homomethyl-N-acetyl anthranilate; salicylic acid-type UV absorbents, such as amyl salicylate, menthyl salicylate, homomethyl salicylate, octyl salicylate, phenyl salicylate, benzyl salicylate, and p-isopropanolphenyl salicylate; cinnamic acid-type UV absorbents, such as octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate(2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, and glyceryl mono-2-ethylhexanoyl-diparamethoxycinnamate; benzophenone-type UV absorbents, such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonic acid salt, 4-phenylbenzophenone, 2-ethylhexyl 4'-phenyl-benzophenone-2-carboxylate, 2-hydroxy-4-n-octoxybenzophenone, and 4-hydroxy-3-carboxybenzophenone; 3-(4'-methylbenzylidene)-d,l-camphor; 3-benzylidene-d,l-camphor; 2-phenyl-5-methylbenzoxazole; 2,2'-hydroxy-5-methylphenyl-benzotriazole; 2-(2'-hydroxy-5'-t-octylphenyl) benzotriazole; 2-(2'-hydroxy-5'-methylphenylbenzotriazole); dibenzaladine; dianisoylmethane; 4-methoxy-4'-t-butyldibenzoylmethane; and 5-(3,3-dimethyl-2-norbornylidene)-3-pentan-2-one.

The metal ion sequestrants includes 1-hydroxyethane-1,1-diphosphonic acid, tetrasodium 1-hydroxyethane-1,1-diphosphonate, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid, and trisodium ethylenediaminehydroxyethyltriacetate.

The lower alcohols include ethanol, propanol, isopropanol, isobutyl alcohol, and t-butyl alcohol.

The polyalcohols include dialcohols, such as ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, and octylene glycol; trialcohols, such as glycerol, and trimethylolpropane; tetralcohols, such as pentaerythritol (e.g., 1,2,6-hexanetriol); pentalcohols, such as xylitol; hexylcohols, such as sorbitol, and mannitol; polyalcohol polymers, such as diethylene glycol, dipropylene glycol, triethylene glycol, polypropylene glycol, tetraethylene glycol, diglycerol, polyethylene glycol, triglycerol, tetraglycerol, and polyglycerol; dialcohol alkyl ethers, such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, and ethylene glycol dibutyl ether; dialcohol alkyl ethers, such as diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether; dialcohol ether esters, such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate; glycerol monoalkyl ethers, such as xylyl alcohol, selachyl alcohol, and batyl alcohol; sugar alcohols, such as sorbitol, maltitol, maltotriose, mannitol, sucrose, erythritol, glucose, fructose, starch amylolysis sugar, maltose, xylitose, and alcohol prepared by reducing starch amylolysis sugar; glysolid; tetrahydrofurfuryl alcohol; POE-tetrahydrofurfuryl alcohol; POP-butyl ether; POP/POE-butyl ether; tripolyoxypropylene glycerol ether; POP-glycerol ether; POP-glycerol ether phosphoric acid; POP/POE-pentaneerythritol ether, and polyglycerol.

The monosaccharides include trioses, such as D-glyceryl aldehyde, and dihydroxy acetone; tetroses, such as D-erythrose, D-erythrulose, D-threose, and erythritol; pentoses, such as L-arabinose, D-xylose, L-lyxose, D-arabinose, D-ribose, D-ribulose, D-xylulose, and L-xylulose; hexoses, such as D-glucose, D-talose, D-psicose, D-galactose, D-fructose, L-galactose, L-mannose, and D-tagatose; heptoses, such as aldoheptose, and hepturose; octoses, such as octurose; deoxysaccharides, such as 2-deoxy-D-ribose, 6-deoxy-L-galactose, and 6-deoxy-L-mannose; aminosaccharides, such as D-glucosamine, D-galactosamine, sailic acid, aminouronic acid, and muramic acid; uronic acids, such as D-glucuronic acid, D-mannuronic acid, L-gulonic acid, D-galacturonic acid, and L-iduronic acid.

The oligosaccharides include sucrose, gunchianose, umbelliferose, lactose, planteose, isolignoses, α,α-trehalose, raffinose, lignoses, umbilicine, stachyose, and belbascose.

The polysaccharides include cellulose, quince seed, chondroitin sulfuric acid, starch, galactan, dermatan sulfate, glycogen, gum arabic, heparan sulfate, hyaluronic acid, gum tragacanth, keratan sulfate, chondroitin, xanthan gum, mucoitin sulfate, guar gum, dextran, kerato sulfate, locust bean gum, succinoglucane, and charonic acid.

The amino acids include neutral amino acids, such as threonine, and cysteine; basic amino acids, such as hydroxylysine. The amino acid derivatives include sodium acylsarcosine (sodium lauroylsarcosine), acylglutamic acid salts, sodium acyl-β-alanine, glutathione, and pyrrolidonecarboxylic acid.

The organic amines include monoethanolamine, diethanolamine, triethanolamine, morpholine, triisopropanolamine, 2-amino-2-methyl-1,3-propanediol, and 2-amino-2-methyl-1-propanol.

The polymer emulsions include acrylic resin emulsion, polyethyl acrylate emulsion, acrylic resin liquid, polyacrylalkyl ester emulsion, polyvinyl acetate resin emulsion, and natural rubber latex.

The pH regulators include buffers, such as lactic acid/sodium lactate, citric acid/sodium citrate, and succinic acid/sodium succinate.

The vitamins include vitamin A, B1, B2, B6, C, E and their derivatives, pantothenic acid and its derivatives, and biotin.

The antioxidants include tocopherols, butylhydroxytoluene(BHT), butylhydroxyanisole(BHA), and gallic acid esters.

The antioxidation promoters include phosphoric acid, citric acid, ascorbic acid, maleic acid, malonic acid, succinic acid, fumaric acid, cephalin, hexametaphosphate, phytic acid, and ethylenediamine-tetraacetic acid.

Other ingredients that may be incorporated in the preparation of the invention are, for example, antiseptics, such as ethylparaben, and butylparaben; antiinflammatory agents, such as glycyrrhizinic acid derivatives, glycyrrhetinic acid derivatives, salicylic acid derivatives, hinokitiol, zinc oxide, and allantoin; skin-whitening agents, such as placenta extract, saxifrage extract, and arbutin; various extracts, such as *Phellodendron* bark, *Coptis japonica, Lithospermum erythrorhizon, Paeonia lactiflora, Swertia japonica*, birch, sage, loquat, ginseng, aloe, Malva sylve, iris, grapes, dove wheat, luffa, lily, saffron, *Cnidium officinale*, shengjiang, *Hypericum erectum, Ononis spinosa*, garlic, red pepper, tangerine peel, *Angelica acutiloba*, and seaweed; activators, such as royal jelly, photosensitive agents, and cholesterol derivatives; blood circulation promoters, such as nonylic acid vanillylamide, benzyl nicotinate, β-butoxyethyl nicotinate, capsaicin, zingerone, cantharis tincture, ichthammol, tannic acid, α-borneol, tocopherol nicotinate, inositol hexanicotinate, cyclandelate, cinnarizine, tolazoline, acetylcholine, verapamil, cepharanthine, and γ-oryzanol; antiseborrheics, such as sulfur, and thiantol; antiinflammatory agents, such as tranexamic acid, and dipotassium glycyrrhizinate.

EXAMPLES

The invention is described more concretely with reference to the following Examples, by which, however, the invention is not limited at all. Unless otherwise specifically indicated, the amount is all in terms of % by mass.

First, the test methods and the evaluation methods employed in the present Examples are described below.

[Stability of Vitamin A Fatty Acid Ester]

The residual ratio of the vitamin A fatty acid ester in a sample is taken as the evaluation index. Specifically, the sample is shielded from light with aluminium foil, stored at 50° C. for 1 month, and then the residual ratio of the vitamin A fatty acid ester in the stored sample relative to the content thereof in the sample before stored is determined through analysis by high-performance liquid chromatography; and the thus-determined residual ratio (%) is taken as the evaluation index. The residual ratio nearer to 100% is better. The samples having a residual ratio of at least 80% are good; and those having a residual ratio of less than 80% are not good.

The condition of the high-performance liquid chromatography for determining the residual ratio is as follows:

Column: C18 column (by Shiseido Co., Ltd.)
Detection: UV 310 nm
Mobile phase: 72% methanol/10% acetonitrile/18% ion-exchanged water/0.5% acetic acid.

[Stability (Emulsion Stability) with the Passage of Time]

The samples stored at 50° C. for 1 month in the above-mentioned vitamin A fatty acid ester stability evaluation test were visually checked for the outward appearance thereof to evaluate the stability (emulsion stability) with the passage of time thereof based on the evaluation standards mentioned below.

(Evaluation Standards)

◯: After the base (sample) production, the appearance did not change with no separation after one month (at 50° C.).
Δ: After the base (sample) production, some separation occurred after one month (at 50° C.).
X: With no sufficient emulsifying capacity, the base (sample) could not be produced.

[Feeling in Use (Feeling of Skin Absorption)]

Ten expert panelists tried each sample (just after preparation) on their face, and evaluated it in point of the skin familiarity or feeling of skin absorption in application thereof, based on the evaluation standards mentioned below.

(Evaluation Standards)

⊙: At least 9 panelists supported good feeling of skin absorption.
◯: From 6 to 8 panelists supported good feeling of skin absorption.
Δ: From 4 to 5 panelists supported feeling of skin absorption.
X: At most 3 panelists supported feeling of skin absorption.

[Feeling in Use (Feeling of Efficacy after Application)]

Ten expert panelists applied each sample (just after preparation) onto their face, and evaluated it in point of the feeling of efficacy after application thereof, based on the evaluation standards mentioned below.

(Evaluation Standards)

⊙: At least 9 panelists supported good feeling of efficacy after application.
◯: From 6 to 8 panelists supported good feeling of efficacy after application.
Δ: From 4 to 5 panelists supported good feeling of efficacy after application.
X: At most 3 panelists supported good feeling of efficacy after application.

Comparative Example 1, Examples 1 to 4

Samples shown in Table 1 below were prepared, and according to the evaluation methods mentioned above, they were evaluated in point of the stability of retinol acetate, the base composition stability (emulsion stability) with the passage of time, and the feeling in use (skin familiarity or feeling of skin absorption, feeling of efficacy after application) thereof. The results are shown in Table 1.

TABLE 1

|  | Com. Ex. 1 | Ex. 1 | Ex. 2 | Ex. 3 | Ex. 4 |
|---|---|---|---|---|---|
| Ion-Exchanged Water | bal. | bal. | bal. | bal. | bal. |
| 1,3-Butylene Glycol | 8 | 8 | 8 | 8 | 8 |
| Xylitol | 3 | 3 | 3 | 3 | 3 |
| Dynamite Glycerin | 8 | 8 | 8 | 8 | 8 |
| Xanthan Gum | 0.2 | 0.2 | 0.2 | 0.2 | 0.2 |
| Self-Emulsifying Glycerin Monostearate [Component (b-3)] | 1.5 | 1.08 | 1.5 | 1.08 | 0.54 |

TABLE 1-continued

|  | Com. Ex. 1 | Ex. 1 | Ex. 2 | Ex. 3 | Ex. 4 |
|---|---|---|---|---|---|
| Sorbitan Tristearate [Component (b-1)] | — | 0.27 | 0.5 | 1.35 | 1.35 |
| PEG40 Stearate [Component (b-2)] | 1.2 | 1.35 | 0.7 | 0.27 | 0.81 |
| Myristyl Myristate | 2 | 2 | 2 | 2 | 2 |
| Stearyl Alcohol [Component (c)] | 0.6 | 0.6 | 0.6 | 0.6 | 0.6 |
| Behenyl Alcohol [Component (c)] | 2.2 | 2.2 | 2.2 | 2.2 | 2.2 |
| Cyclomethicone | 2 | 2 | 2 | 2 | 2 |
| Pentaerythritol Tetra-2-ethylhexanoate | 15 | 15 | 15 | 15 | 15 |
| Retinol Acetate [Component (a)] | 0.2 | 0.2 | 0.2 | 0.2 | 0.2 |
| 4-Methoxysalicylic Acid Salt | 1 | 1 | 1 | 1 | 1 |
| Tranexamic Acid | 1 | 1 | 1 | 1 | 1 |
| Citric Acid | 0.04 | 0.04 | 0.04 | 0.04 | 0.04 |
| Sodium Citrate | 0.06 | 0.06 | 0.06 | 0.06 | 0.06 |
| Butylhydroxytoluene (BHT) | 0.05 | 0.05 | 0.05 | 0.05 | 0.05 |
| Trisodium Edetate | 0.05 | 0.05 | 0.05 | 0.05 | 0.05 |
| Phenoxyethanol | 0.5 | 0.5 | 0.5 | 0.5 | 0.5 |

TABLE 1-continued

|  | Com. Ex. 1 | Ex. 1 | Ex. 2 | Ex. 3 | Ex. 4 |
|---|---|---|---|---|---|
| Total Amount of Component (b) (mas %) | 2.7 | 2.7 | 2.7 | 2.7 | 2.7 |
| Component (b-1)/Component (b) (ratio by mass) | — | 0.10 | 0.185 | 0.50 | 0.50 |
| Amount of Component (c) (mas %) | 2.8 | 2.8 | 2.8 | 2.8 | 2.8 |
| Retinol Acetate Residual Ratio (50° C., 1 month, %) | 77.1 | 84.1 | 83.8 | 86.3 | 86 |
| Stability | X | ◯ | ◯ | ◯ | ◯ |
| Stability (emulsion stability) with the passage of time | ◯ | ◯ | ◯ | ◯ | ◯ |
| Feeling in use (feeling of skin absorption) | Δ | ◯ | ◯ | ◯ | ⊙ |
| Feeling in use (feeling of efficacy after application) | Δ | ◯ | ◯ | ⊙ | ⊙ |

As obvious from the results shown in Table 1, Comparative Example 1 not containing component (b-1) had a retinol acetate residual ratio of less than 80%, and its feeling in use was poor.

Examples 5 to 8, Comparative Examples 2 to 4

Samples shown in Table 2 below were prepared, and according to the evaluation methods mentioned above, they were evaluated in point of the stability of retinol acetate, the base composition stability (emulsion stability) with the passage of time, and the feeling in use (skin familiarity or feeling of skin absorption, feeling of efficacy after application) thereof. The results are shown in Table 2.

TABLE 2

|  | Com. Ex. 2 | Ex. 5 | Ex. 6 | Ex. 7 | Ex. 8 | Com. Ex. 3 | Com. Ex. 4 |
|---|---|---|---|---|---|---|---|
| Ion-Exchanged Water | bal. | bal. | bal. | bal. | bal. | bal. | bal. |
| 1,3-Butylene Glycol | 8 | 8 | 8 | 8 | 8 | 8 | 8 |
| Xylitol | 3 | 3 | 3 | 3 | 3 | 3 | 3 |
| Dynamite Glycerin | 8 | 8 | 8 | 8 | 8 | 8 | 8 |
| Xanthan Gum | 0.2 | 0.2 | 0.2 | 0.2 | 0.2 | 0.2 | 0.2 |
| Self-Emulsifying Glycerin Monostearate [Component (b-3)] | 2.4 | 1.5 | 1.2 | 0.9 | 0.6 | 0.3 | 0.15 |
| Sorbitan Tristearate [Component (b-1)] | 0.8 | 0.5 | 0.4 | 0.3 | 0.2 | 0.1 | 0.05 |
| PEG40 Stearate [Component (b-2)] | 1.12 | 0.7 | 0.56 | 0.42 | 0.28 | 0.14 | 0.07 |
| Myristyl Myristate | 2 | 2 | 2 | 2 | 2 | 2 | 2 |
| Stearyl Alcohol [Component (c)] | 0.6 | 0.6 | 0.6 | 0.6 | 0.6 | 0.6 | 0.6 |
| Behenyl Alcohol [Component (c)] | 2.2 | 2.2 | 2.2 | 2.2 | 2.2 | 2.2 | 2.2 |
| Cyclomethicone | 2 | 2 | 2 | 2 | 2 | 2 | 2 |
| Pentaerythritol Tetra-2-ethylhexanoate | 15 | 15 | 15 | 15 | 15 | 15 | 15 |
| Retinol Acetate [Component (a)] | 0.2 | 0.2 | 0.2 | 0.2 | 0.2 | 0.2 | 0.2 |
| 4-Methoxysalicylic Acid Salt | 1 | 1 | 1 | 1 | 1 | 1 | 1 |
| Tranexamic Acid | 1 | 1 | 1 | 1 | 1 | 1 | 1 |
| Citric Acid | 0.04 | 0.04 | 0.04 | 0.04 | 0.04 | 0.04 | 0.04 |
| Sodium Citrate | 0.06 | 0.06 | 0.06 | 0.06 | 0.06 | 0.06 | 0.06 |
| Butylhydroxytoluene (BHT) | 0.05 | 0.05 | 0.05 | 0.05 | 0.05 | 0.05 | 0.05 |
| Trisodium Edetate | 0.05 | 0.05 | 0.05 | 0.05 | 0.05 | 0.05 | 0.05 |
| Phenoxyethanol | 0.5 | 0.5 | 0.5 | 0.5 | 0.5 | 0.5 | 0.5 |
| Total Amount of Component (b) (mas %) | 4.32 | 2.7 | 2.16 | 1.62 | 1.08 | 0.54 | 0.27 |
| Component (b-1)/Component (b) (ratio by mass) | 0.185 | 0.185 | 0.185 | 0.185 | 0.185 | 0.185 | 0.185 |
| Amount of Component (c) (mas %) | 2.8 | 2.8 | 2.8 | 2.8 | 2.8 | 2.8 | 2.8 |
| Retinol Acetate Residual Ratio (50° C., 1 month, %) | 76 | 83.8 | 83.2 | 85.3 | 87.3 | — | — |
| Stability | X | ◯ | ◯ | ◯ | ◯ | — | — |
| Stability (emulsion stability) with the passage of time | ◯ | ◯ | ◯ | ◯ | ◯ | Δ | X |
| Feeling in use (feeling of skin absorption) | ⊙ | ◯ | ◯ | ◯ | Δ | Δ | — |
| Feeling in use (feeling of efficacy after application) | ⊙ | ◯ | ◯ | ◯ | Δ | Δ | — |

As obvious from the results shown in Table 2, in Comparative Example 2 in which the total amount of component (b) is over the range of the invention, the stability of retinol acetate was poor. Comparative Examples 3 and 4 in which the total amount of component (b) is less than the range of the invention had poor base composition stability (emulsion stability) with the passage of time; Comparative Example 3 showed some phase separation after one month (50° C.) after cream base production; and in Comparative Example 4, cream base production was impossible. In Comparative Examples 3 and 4, the retinol acetate residual ratio could not be determined.

Examples 9 to 11

Samples shown in Table 3 below were prepared, and according to the evaluation methods mentioned above, they were evaluated in point of the base composition stability of retinol acetate, the stability (emulsion stability) with the passage of time, and the feeling in use (skin familiarity or feeling of skin absorption, feeling of efficacy after application) thereof. The results are shown in Table 3.

TABLE 3

|  | Ex. 9 | Ex. 10 | Ex. 11 |
|---|---|---|---|
| Ion-Exchanged Water | bal. | bal. | Bal. |
| 1,3-Butylene Glycol | 8 | 8 | 8 |
| Xylitol | 3 | 3 | 3 |
| Dynamite Glycerin | 8 | 8 | 8 |
| Xanthan Gum | 0.2 | 0.2 | 0.2 |
| Self-Emulsifying Glycerin Monostearate [Component (b-3)] | 0.48 | 0.32 | 0.16 |
| Sorbitan Tristearate [Component (b-1)] | 0.66 | 0.98 | 1.3 |
| PEG40 Stearate [Component (b-2)] | 0.48 | 0.32 | 0.16 |
| Myristyl Myristate | 2 | 2 | 2 |
| Stearyl Alcohol [Component (c)] | 0.9 | 0.9 | 0.9 |
| Behenyl Alcohol [Component (c)] | 3.3 | 3.3 | 3.3 |
| Cyclomethicone | 2 | 2 | 2 |
| Pentaerythritol Tetra-2-ethylhexanoate | 15 | 15 | 15 |
| Polypropylene Polymer | 1 | 1 | 1 |
| Retinol Acetate [Component (a)] | 0.2 | 0.2 | 0.2 |
| 4-Methoxysalicylic Acid Salt | 1 | 1 | 1 |
| Tranexamic Acid | 1 | 1 | 1 |
| Citric Acid | 0.04 | 0.04 | 0.04 |
| Sodium Citrate | 0.06 | 0.06 | 0.06 |
| Butylhydroxytoluene (BHT) | 0.05 | 0.05 | 0.05 |
| Trisodium Edetate | 0.05 | 0.05 | 0.05 |
| Phenoxyethanol | 0.5 | 0.5 | 0.5 |
| Total Amount of Component (b) (mas %) | 1.62 | 1.62 | 1.62 |
| Component (b-1)/Component (b) (ratio by mass) | 0.41 | 0.61 | 0.80 |
| Amount of Component (c) (mas %) | 4.2 | 4.2 | 4.2 |
| Retinol Acetate Residual Ratio (50° C., 1 month, %) | 89.5 | 90.1 | 88.4 |
| Stability | ◯ | ◯ | ◯ |
| Stability (emulsion stability) with the passage of time | ◯ | ◯ | ◯ |
| Feeling in use (feeling of skin absorption) | ⊙ | ◯ | ◯ |
| Feeling in use (feeling of efficacy after application) | ⊙ | ⊙ | ◯ |

As obvious from the results shown in Table 3, Examples 9 to 11 in which components (a) to (c) were within the scope of the invention were excellent in the stability of retinol acetate, in the base composition stability (emulsion stability) with the passage of time, and in the feeling in use (skin familiarity or feeling of skin absorption, feeling of efficacy after application).

Formulation Examples are shown below.

Example 12

Skin Cream

| (Ingredients) | (mas %) |
|---|---|
| (1) Retinol Acetate | 0.2 |
| (2) Sorbitan Tristearate | 1.35 |
| (3) PEG40 Stearate | 0.81 |
| (4) Self-Emulsifying Glycerin Monostearate | 0.54 |
| (5) Stearyl Alcohol | 0.9 |
| (6) Behenyl Alcohol | 3.3 |
| (7) Pentaerythritol Tetra-2-ethylhexanoate | 15 |
| (8) Cyclomethicone | 2 |
| (9) Myristyl Myristate | 2 |
| (10) BHT | 0.05 |
| (11) Sodium Pyrosulfite | 0.003 |
| (12) Dynamite Glycerin | 8 |
| (13) Xylitol | 3 |
| (14) 1,3-Butylene Glycol | 8 |
| (15) Xanthan Gum | 0.2 |
| (16) Sodium Citrate | 0.06 |
| (17) Citric Acid | 0.04 |
| (18) Trisodium Edetate | 0.05 |
| (19) Phenoxyethanol | 0.5 |
| (20) Tranexamic Acid | 1 |
| (21) Potassium 4-Methoxysalicylate | 1 |
| (22) Water | bal. |

(Production Method)

(1) to (10) are uniformly mixed and dissolved at 70° C. (oily phase). On the other hand, (11) to (22) are uniformly mixed and dissolved at 70° C. (aqueous phase). The oily phase is added to the aqueous phase kept at 70° C., and emulsified with a homomixer. After the emulsification, this is cooled to 30° C.

INDUSTRIAL APPLICABILITY

The oil in water emulsion cosmetic composition for skin of the invention secures stable incorporation of vitamin A and its derivatives therein and is excellent in the feeling in use (skin familiarity or feeling of skin absorption, feeling of efficacy after application) and in the base composition stability (emulsion stability) with the passage of time.

The invention claimed is:

1. An oil in water emulsion cosmetic composition for skin comprising, relative to the total amount of the cosmetic composition,
   (a) from 0.01 to 4% by mass of vitamin A and its derivative;
   (b) from 0.6 to 4% by mass of a nonionic surfactant comprising the following components (b-1) to (b-3):
      (b-1) sorbitan tristearate,
      (b-2) polyethylene glycol stearate with from 20 to 120 mols of polyethylene glycol added thereto,
      (b-3) glyceryl stearate having an HLB of from 5 to 8,
   (c) from 1 to 10% by mass of a higher alcohol having from 14 to 24 carbon atoms;
   wherein the blend ratio (by mass) of component (b-1) to component (b) is from 0.1 to 0.8.

2. The oil in water emulsion cosmetic composition for skin as claimed in claim 1, wherein component (a) is a vitamin A fatty acid ester and its salt.

3. The oil in water emulsion cosmetic composition for skin as claimed in claim 2, wherein component (c) is a stearyl alcohol.

4. The oil in water emulsion cosmetic composition for skin as claimed in claim 2, wherein component (c) is a behenyl alcohol.

5. The oil in water emulsion cosmetic composition for skin as claimed in claim 2, wherein component (c) is a stearyl alcohol and a behenyl alcohol.

6. The oil in water emulsion cosmetic composition for skin as claimed in claim 1, wherein component (c) is a stearyl alcohol.

7. The oil in water emulsion cosmetic composition for skin as claimed in claim 1, wherein component (c) is a behenyl alcohol.

8. The oil in water emulsion cosmetic composition for skin as claimed in claim 1, wherein component (c) is a stearyl alcohol and a behenyl alcohol.

9. The oil in water emulsion cosmetic composition for skin as claimed in claim 1, wherein an aqueous phase of the cosmetic composition is from 20 to 80% by mass relative to the total amount of the cosmetic composition.

10. The oil in water emulsion cosmetic composition for skin as claimed in claim 1, wherein an aqueous phase of the cosmetic composition is from 30 to 60% by mass relative to the total amount of the cosmetic composition.

11. The oil in water emulsion cosmetic composition for skin as claimed in claim 1, wherein the blend ratio (by mass) of component (b-1) to component (b) is from 0.41 to 0.80.

12. The oil in water emulsion cosmetic composition for skin as claimed in claim 1, wherein the component (a) is at least one selected from a group consisting of retinol, retinal, retinoic acid, vitamin A fatty acid ester and their salts.

13. The oil in water emulsion cosmetic composition for skin as claimed in claim 1, wherein the component (a) is vitamin A fatty acid ester.

14. The oil in water emulsion cosmetic composition for skin as claimed in claim 1, wherein the component (a) is retinol acetate.

15. The oil in water emulsion cosmetic composition for skin as claimed in claim 1, wherein a content of the component (c) by mass relative to the total amount of the cosmetic composition is greater than a content of the component (b) by mass relative to the total amount of the cosmetic composition.

* * * * *